(12) United States Patent
Cailly-Dufestel et al.

(10) Patent No.: US 8,501,160 B2
(45) Date of Patent: Aug. 6, 2013

(54) CRUSH-RESISTANT OXYCODONE TABLETS INTENDED FOR PREVENTING ACCIDENTAL MISUSE AND UNLAWFUL DIVERSION

(75) Inventors: Vincent Cailly-Dufestel, Bosc-Guérard-Saint-Adrien (FR); Catherine Herry, Saint Pierre lès Elbeuf (FR); Johnatan Bacon, Montreal (CA); Pascal Oury, Le Chesnay (FR)

(73) Assignee: Ethypharm SA, Houdan (FR)

( * ) Notice: Subject to any disclaimer, the term of this patent is extended or adjusted under 35 U.S.C. 154(b) by 1310 days.

(21) Appl. No.: 12/224,385

(22) PCT Filed: Mar. 1, 2007

(86) PCT No.: PCT/EP2007/051969
§ 371 (c)(1),
(2), (4) Date: Aug. 26, 2008

(87) PCT Pub. No.: WO2007/099154
PCT Pub. Date: Sep. 7, 2007

(65) Prior Publication Data
US 2009/0011016 A1    Jan. 8, 2009

(30) Foreign Application Priority Data
Mar. 1, 2006   (FR) ...................................... 06 01842

(51) Int. Cl.
*A61K 9/44*   (2006.01)
(52) U.S. Cl.
USPC ........................................................ 424/10.2
(58) Field of Classification Search
CPC ........................................................ A61K 9/44
See application file for complete search history.

(56) References Cited

U.S. PATENT DOCUMENTS

| | | | |
|---|---|---|---|
| 3,773,955 A | 11/1973 | Pachter et al. | |
| 3,966,940 A | 6/1976 | Pachter et al. | |
| 4,874,614 A * | 10/1989 | Becker | 424/465 |
| 5,725,886 A * | 3/1998 | Erkoboni et al. | 424/499 |
| 5,747,058 A | 5/1998 | Tipton et al. | |
| 6,413,536 B1 | 7/2002 | Gibson et al. | |
| 6,592,901 B2 | 7/2003 | Durig et al. | |
| 2001/0038852 A1 * | 11/2001 | Kolter et al. | 424/465 |
| 2003/0004177 A1 * | 1/2003 | Kao et al. | 514/282 |
| 2003/0064099 A1 * | 4/2003 | Oshlack et al. | 424/465 |
| 2003/0068392 A1 | 4/2003 | Sackler | |
| 2003/0118641 A1 | 6/2003 | Maloney et al. | |
| 2003/0143269 A1 | 7/2003 | Oshlack et al. | |
| 2005/0031546 A1 | 2/2005 | Bartholomaus et al. | |
| 2005/0281748 A1 | 12/2005 | Hirsh et al. | |
| 2006/0002859 A1 * | 1/2006 | Arkenau et al. | 424/10.1 |

FOREIGN PATENT DOCUMENTS

| | | |
|---|---|---|
| EP | 0 185 472 B1 | 6/1986 |
| EP | 0 319 243 B1 | 6/1989 |
| EP | 0 933 079 B1 | 8/1999 |
| EP | 0 974 355 B1 | 1/2000 |
| EP | 0 997 143 A1 | 5/2000 |

OTHER PUBLICATIONS

Pontier, et al.; "Use of cycles of compression to characterize the behaviour of apatitic phosphate powders"; Journal of the European Ceramic Society 22 (2002) 1205-1216.
Fell, et al.; "Determination of Tablet Strength by the Diametral-Compression Test; Journal al Pharmaceutical Sciences"; vol. 59, No. 5 (May 1970).
OxyContin: Questions and Answers; http://www.fda.gov/cder/drug/infopage/oxycontin/oxycontin-qa.htm; 3 pgs.; created Aug. 2, 2001.
Pointier; Thesis research on Apatitic calcium phosphate compression ("Les phosphates de calcium apatitiques en compression. De la chimie aux qualites d'usage"These de l'Universite de Paris XI, presented on Sep. 25, 2001 (Abstract only).

* cited by examiner

*Primary Examiner* — Michael G Hartley
*Assistant Examiner* — Melissa Perreira
(74) *Attorney, Agent, or Firm* — Foley & Lardner LLP

(57) ABSTRACT

Water-insoluble matrix tablets based on oxycodone or one of its pharmaceutically acceptable salts and capable of prolonged release of oxycodone to the body, exhibiting a crush resistance of at least 4 MPa.

13 Claims, 9 Drawing Sheets

Dissolution profiles at pH 6.8 of non-film coated 40 mg oxycodone HCl tablets, obtained according to Example 1.

Dissolution profiles at pH 6.8 of non-film coated 40 mg oxycodone HCl tablets, obtained according to Example 2.

Dissolution profile at pH 6.8 of tablets conforming to Example 2, film-coated with a layer of Ethylcellulose EC30 D and subjected to a curing step Comparative dissolution profiles of oxycodone matrix tablets conforming to the invention in an ethanol-free 0.1 N HCl medium and in a 0.1 N HCl medium containing 40 % ethanol Dissolution profiles of oxycodone matrix tablets conforming to the invention in two dissolution media of different pH (1.2 and 6.8)

24-hour dissolution profiles of 40 mg oxycodone tablets conforming to the invention after a storage period in Al/Al blister pack under accelerated stability conditions of 1 month, 2 months, 3 months and 6 months.

24-hour dissolution profiles of 20 mg oxycodone tablets conforming to the invention after a storage period in HDPE bottles with desiccant under accelerated stability conditions of 1 month, 2 months and 3 months.

Plasma profiles of oxycodone after once-a-day administering of 40 mg oxycodone tablets conforming to the invention, and 40 mg oxycodone tablets of the reference product Oxycontin®

24-hour dissolution profile of ultra-hard non-coated tablets containing oxycodone and naloxone, at pH 6.8.

10-hour dissolution profiles at pH 6.8 of ultra-hard, non-coated 20 mg oxycodone tablets comprising a matrix containing mineral excipients Dissolution profiles of tablets conforming to the invention(« QD ») and tablets of the reference product Oxycontin® (ref) at pH 6.8, for whole tablets, tablets cut in half, or crushed (« in pieces »)

CRUSH-RESISTANT OXYCODONE TABLETS INTENDED FOR PREVENTING ACCIDENTAL MISUSE AND UNLAWFUL DIVERSION

The present invention concerns insoluble matrix tablets having very high crush resistance.

These matrix tablets which are unbreakable under usual conditions, non-friable and insoluble in an aqueous medium, are of particular interest as reservoirs for psychotropic agents since they can reduce and even prevent addictive abuse of these substances by crushing, dissolving and injection, or by crushing and inhalation.

The present invention also concerns the method to obtain said tablets and their use for sustained-release oral administering of the active ingredients, and in particular of psychotropic active ingredients.

With respect to tablets containing sustained-release opiate agents, in particular oxycodone, the phenomenon of accidental misuse may assume several aspects. First, it may arise from failure to heed administering conditions. It may happen that the tablet, intended to be swallowed, is accidentally chewed by the patient. The consequences of full or partial destruction of the tablet whose structure is intended to delay the release of the active ingredient, can prove to be dangerous and even fatal for the patient (excess dosage leading overdose). This is the reason why the leaflet supplied with the drug OxyContin® LP specifically states that « The tablets must be swallowed whole without being chewed » .

Also, accidental misuse of drugs containing sustained-release oxycodone has also been observed when patients simultaneously, or within a short time interval, ingest the drug with a strong dose of alcohol.

It has effectively been observed with a sustained-release form of hydromorphone that the presence of alcohol in the stomach deteriorated the layer of excipients designed for sustained release of the active ingredient, leading to release into the body of a major quantity of active ingredient («dose-dumping» ), once again the cause of a dangerous overdose.

The leaflet supplied with OxyContin® LP for example indicates in the list of contraindications that the consumption of alcohol is to be avoided with this drug.

Similarly, in the United States, the FDA (Food and Drug Administration) gives a serious warning to patients treated with OxyContin® not to consume alcoholic drinks during the period of treatment (see in particular: http://www.fda.gov/cder/drug/infopage/oxycontin/oxycont in-qa.htm).

There is therefore a real need to prevent this type of accidental misuse to increase patient safety, whilst maintaining a simple, comfortable route of administration (oral route).

Since the placing on the French pharmaceutical market in 1990 of substitute treatments for opiate drugs, in the form of sublingual tablets (Temgésic®) initially packed in a form for injection, an increase has been observed in the phenomenon of abuse of certain psychotropic agents by drug addicts.

The term deliberate misuse or illicit use (or more usually "drug-abuse") is used to qualify the use of certain medicinal products for addiction purposes, in particular the use of certain psychotropic or narcotic agents e.g. opioids or their derivatives intended to treat severe pain or to treat addiction to opiate drugs.

Abuse by parenteral/nasal route of sustained-release active ingredients normally intended for oral route, gives drug addicts the opportunity to achieve immediate, accumulated psychotropic effects of the total active ingredient dose present in the initial formulation.

For example, in the particular case of buprenorphine, a powerful opioid analgesic initially sold as a preparation under the name Temgesic® for the substitution treatment of drug addiction, it is estimated that 25% to 30% of the treatments sold are given abuse by parenteral or nasal route. The same applies to the preparation called Subutex® (sublingual tablets with high buprenorphine dosage manufactured by Schering-Plough) officially used as substitution treatment in tens of thousands of opioid drug addicts, for which it is estimated that 34% of consumers abuse the drug by injection and approximately 30% by nasal route.

Yet the phenomenon of drug abuse is also seen with preparations intended to treat severe pain, such as morphine sulphate (Skenan®) and oxycodone for example (Moscontin®, OxyContin® LP) or moderate pain (Neocodion®). These sustained-release forms contain large quantities of opioids intended to limit pain over long periods, and abuse thereof gives rise to the massive release of morphine derivatives.

Drug abuse also affects other classes of therapeutic drugs, in particular benzodiazepines (Rohypnol®), and to a lesser extent certain neurological treatments (Artane® Antiparkinson drug).

As a result, these therapeutic or substitution treatments, in some cases accessible by mere prescription, and whose dosage can reach up to ten or so tablets a day, are subject to two chief modes of abuse: parenteral administration (injection) and nasal administration (inhalation).

With regard to abuse by injection, the tablet or capsule containing the active ingredients of interest is reduced to a fine powder using any possible means available to the drug addict, in particular a mortar or lighter, even simply by chewing or biting the tablet. The rough powder obtained, which necessarily contains the excipients initially present in the pharmaceutical form, can then be dissolved in a small volume of liquid (a few millilitres) sometimes previously heated and/or to which an acid is added for certain active ingredients present in base form (brown heroin, base morphine). The liquid obtained can then be roughly filtered to limit the entry of large particles into the bloodstream, using a cigarette filter for example, before it is injected via intravenous route.

In this case, the active ingredient then becomes immediately available in the bloodstream, since there is no longer any excipient to delay its release, giving rise to an immediate psychotropic effect sought by drug addicts.

Abuse by inhalation also consists of crushing the pharmaceutical form until a sufficiently fine powder is obtained to render the active ingredient accessible to the micro-vessels of the intranasal mucous membrane. Here again, the action of the sustained-release excipients, designed for oral administration, is fully ineffective and the expected immediate psychotropic effect is able to be achieved.

Drug abuse is also accompanied by numerous health risks related directly to injection or inhalation of the excipients and of non-purified crush residues, little or ill-filtered and non-sterile. Recent studies report that some tampered tablets are sometimes dissolved directly in the syringe, then injected without any prior filtering, this practice being directly responsible for numerous deaths through pulmonary embolism. Additionally, the addition of acids in non-sterile liquid form (lemon juice) to the crush residues is apparently also responsible for the transmission of bacterial or mycosal pathologies (candidiasis).

These practices therefore come to increase the already high risks of viral and bacterial transmissions and complications of dermatological type (abscesses, necrosis) related to the parenteral injection itself. Also, regarding the injection of Subutex® tablets, the presence of corn starch in the tablet formulation is responsible for the onset of oedema due to this excipient which, once injected, accumulates in the lymph and venous systems leading to swelling of the lower limbs.

To limit these problems, one approach consists of associating the active ingredient in one same pharmaceutical form with an agent capable of limiting the psychotropic effect when the formulation is taken by parenteral route.

This is the case for example with formulations combining methadone and naloxone, initially described in patents U.S. Pat. No. 3,966,940 and U.S. Pat. No. 3,773,955.

This abuse-deterrent formulation was reproduced in the particular case of buprenorphine. Patent EP 0 185 472 for example describes an oral formulation of buprenorphine also containing an effective dose of naloxone, which acts as competing antagonist at the morphone receptors. Since naloxone has only very slight bio-availability via oral route, it little hinders the analgesic action of buprenorphine when the medicinal product is administered conventionally per os. On the other hand, when subject to abuse by parenteral route, naxolone becomes fully available and inhibits the analgesic action of buprenorphine. With this type of chemical association, however, the oral pharmaceutical form remains crushable and soluble in an aqueous medium.

One sublingual formulation combining naltrexone with buprenorphine has also been described in patent EP 0 319 243. With said association, it is possible in particular to increase the antagonist effect of naltrexone with respect to opioids, whilst providing consumers with a non-euphorigenic, analgesic sensation even if the composition is abused by parenteral route. This type of formulation therefore has little appeal for a drug addict and contributes towards curbing the phenomenon of drug abuse. However, this approach necessarily has recourse to the co-administering of two active ingredients, leading to increased production costs and sale price of the medicinal product.

Still using an approach combining the association of the opioid with an antagonist agent, patent application US 2003/0143269 describes a pharmaceutical form in which the opioid and the antagonist are interdispersed so that the antagonist is "sequestered" in a compartment preventing it from being released when the medicinal product is taken normally by oral route. On the other hand, if the product is tampered with by crushing, deterioration of the structure leads to mixing of the two active agents and to inhibition of the sought after psychotropic effect.

In this approach, the pharmaceutical form has a predominant role to play against abuse. However, here again the chemical association of two compounds is necessary, leading to a complex manufacturing process and high production costs.

Also, patent application US 2003/0068392 describes a pharmaceutical form in which the opioid agent is associated not only with an antagonist, but also with an irritant agent sequestered in a closed compartment. Tampering with the pharmaceutical form inevitably leads to release of the irritant. This form therefore requires the association of three active agents, and the creation of compartmented areas, which makes its manufacture complex and more costly than a simple pharmaceutical form such as a tablet.

Other companies have developed pharmaceutical systems in which the opioid or substance which may be subject to abuse is not associated with an antagonist. For example, patent application US 2005/0281748 teaches the manufacture of an oral dosage pharmaceutical form in which the opioid agent of interest is modified so as to increase its lipophilicity, by forming a salt between the active agent and one or more fatty acids.

This pharmaceutical form allows the sustained release of the active ingredient when it is taken by oral route, since the enzymes of the gastrointestinal tract gradually break down the groups of fatty acids, releasing the active ingredient as and when they are broken down.

On the other hand, any physical tampering of the pharmaceutical form releases microparticles of active ingredient coated with an insoluble layer, preventing the immediate release of the active ingredient in an aqueous medium. Said formulation requires chemical conversion of the active ingredient.

Patent application US 2003/0118641 describes an oral dosage form of opioid with sustained release, in which the active opioid ingredient is associated with a hydrophilic polymer matrix and a cationic resin. Since the resin carries opposite charges to the active ingredient, it binds to this ingredient within the polymer matrix, preventing its extraction.

Said pharmaceutical form renders the active compound inseparable from the excipients responsible for its sustained release in the body, even if usually available solvents are used (hot water, alcohol, vinegar, hydrogen peroxide, etc . . . ).

Some companies have developed pharmaceutical systems containing gels. For example Pain Therapeutics Inc. and Durect use a biodegradable gel which can be administered via oral or parenteral route, consisting of an agent with high viscosity: Sucrose Acetate Iso Butyrate (SAIB). This gel allows sustained release of an opioid agent, oxycodone. This type of gel, which is the subject of patents U.S. Pat. No. 5,747,058 and U.S. Pat. No. 6,413,536 maintains its capacity to release the active ingredient controllably over periods of 12 to 24 hours, even if the capsules containing the same are deteriorated or crushed. The main interest of these pharmaceutical forms lies in the fact that the oxycodone cannot be extracted from its gel carrier, and cannot be injected either via parenteral route owing to the very high viscosity of these formulations (Remoxy® product using ORADUR® and SABER® technologies currently undergoing phase III clinical trials).

Said gels also have the capacity to resist extraction of oxycodone in the presence of an alcohol or acid, the active ingredient remaining trapped in the network formed by the gelling agent.

These gel-containing pharmaceutical forms are complex formulations, which firstly require the use of high viscosity liquids at industrial level, giving rise to restricted handling, and secondly entail major restrictions with regard to packaging (use of bottles of vials), which is not the case with tablets.

Means are also known with which to manufacture matrix tablets of very high hardness. Patent EP 0 974 355 describes tablets obtained by granulating a hydrosoluble vitamin mixed with at least one additive of saccharide type, in the presence of a conventional polymer binder such as HPMC for example. Said tablets, intended for swift release of the hydrosoluble vitamin in the body, have high hardness strength, in the order of 20 to 30 kp/cm$^2$ (kiloponds/cm$^2$), which is equivalent to hardness values of approximately 1.96 to 2.94 MPa. Although relatively hard and consisting of more than 90% hydrosoluble vitamin and of excipients that are also hydrosoluble (HPMC, saccharides), these tablets disintegrate rapidly in the body (disintegration time in the region of 10 to 15 minutes). Said tablets are firstly fully unsuitable for sustained release of the active ingredient, and secondly are easily dissolved in an aqueous medium, making them unfit for use as pharmaceutical form for substances which may be given abuse.

Patent EP 0 933 079 describes matrix tablets having a crush resistance varying from around 1 MPa (1 N/mm$^2$) up to 10 MPa. Said tablets are obtained from a treated starch powder that can be directly compressed. However, these tablets are intended for the rapid release of active ingredients, since they have a relatively short disintegration time in an aqueous medium, in the order of approximately 6 to 7 minutes. Owing to their rapid disintegration in an aqueous medium these tablets, here again, cannot be used to convey active ingredients which are liable to be given abuse and which are intended to be released over long time periods.

Patent EP 0 997 143 describes the production of bi-convex matrix tablets of very high hardness (up to 1.1 MPa i.e. around 11 kp/cm$^2$) and with a friability of less than 1%, obtained after compressing a matrix consisting chiefly of a compressible, disintegratable carbohydrate (generally mannitol) and a binder. Said chewable tablets, even if they have very high hardness in the solid state, dissolve in an aqueous medium and after a very short period of time in the mouth, and therefore rapidly release the active ingredient into the body.

The manufacture of matrix tablets intended for the sustained release of an active substance in the body, and also having high hardness, is taught by patent U.S. Pat. No. 6,592,901. In this document, tablets are obtained having good compressibility characteristics and containing a particular grade of ethylcellulose (non-ionic ethyl ether of cellulose—sold under the trade name Aqualon®), that is pH-independent, highly substituted and of low viscosity. The crush resistance of the tablets thus obtained is in the order of 10 to 20 kp (kiloponds) which, scaled down to the size of tablets, is equivalent to around 1.4-2.8 MPa. Also, this special grade of ethylcellulose is water-insoluble, limiting the diffusion of liquids and hence release of the active ingredient in the body. Release of the active ingredient is achieved slowly since the tablets obtained from this model show a release profile in which less than 80% of the active ingredient is released after 24 hours.

Matrix tablets having very strong crush resistance are also described in the work by Pontier et al. (Pontier et al. *Journal of European Ceramic Society*, 22 (2002)). In particular, the authors show that it is possible to obtain very hard matrix tablets using mineral excipients of the calcium phosphate family, such as tricalcium phosphate or hydroxyapatite, by direct compression. For example, from a tricalcium phosphate powder, previously granulated then compressed under compression forces in the order of 300 MPa, it is possible to obtain tablets whose crush resistance (tensile strength) can reach 6.5 MPa. However, this article does not give any information on the capacity of such tablets to release one or more active ingredients over an extended period of time, nor the capacity of such pharmaceutical structures to remain intact in an aqueous medium.

Thesis research on apatitic calcium phosphate compression by C. Pontier ("*Les phosphates de calcium apatitiques en compression. De la chimie aux qualités d'usage*" Thèse de l'Université de Paris XI, presented on 25 Sep. 2001) shows that it is possible, after compression, to obtain matrix tablets containing calcium phosphates (hydroxyapatite and tricalcium phosphate in particular), having very high crush resistance possibly reaching 7 MPa.

Said tablets also have the capability of releasing theophylline in an aqueous medium over a long period of time (60% of active ingredient released in 8 hours) by gradual diffusion through the matrix pores. However, this article does not allow any conclusion to be drawn on the capacities of said tablets to remain intact in an aqueous medium, and hence to resist abuse by crushing in a liquid medium.

Patent application US 2005/0031546 concerns an abuse-deterrent pharmaceutical form containing one or more active ingredients liable to give rise to addiction, and at least one synthetic or natural polymer necessarily having a tensile strength of at least 500 N. The only polymer specifically described is ethylene polyoxide having a molecular weight of 7 000 000 optionally associated with an xanthane gum. These tablets can be prepared using a method which comprises a compression step preceded by a heat exposure step, concomitant with a heat exposure step or followed by a heat exposure step. Therefore the heat exposure step is necessary to obtain the desired hardness. This step, even if of short duration, is firstly not applicable to heat-sensitive active ingredients and secondly requires the use of special equipment and extra energy consumption which contributes towards increasing the cost of the process.

There is therefore a true need for the development of a pharmaceutical form which allows the safe administering of active ingredients having a psychotropic effect and which are released over an extended period of time i.e. which has a pharmaceutical structure which makes both its crushing and its dissolution highly difficult or even impossible, and further which prevents the extraction and separation of the active ingredient from the agents responsible for its sustained release. In addition, it must be possible for this pharmaceutical form to be produced using an extremely simple manufacturing method, that is rapid and low cost.

The applicant has unexpectedly found a novel, solid, oral pharmaceutical formulation prepared simply in the form of sustained-release matrix tablets, that are both insoluble and ultra-hard. With said tablets, it is possible to prevent the phenomenon of accidental misuse and to curb and even eliminate the phenomenon of drug abuse.

The subject-matter of the invention is therefore water-insoluble matrix tablets, capable of releasing one or more active ingredients into the body over extended periods, preferably over periods of more than 12 hours and further preferably more than 20 hours, containing oxycodone dispersed in a compression matrix, said matrix consisting of at least one excipient chosen from the group comprising sustained-release, water-insoluble, pH-independent polymers, mineral excipients and their mixtures, the quantity of said excipient and the compression conditions being chosen so that said tablets have a crush resistance of at least 4 MPa, advantageously at least 6 MPa.

Advantageously, the compression conditions do not necessarily entail a heating step of the mixture to be compressed, or of the compression tooling either before or during the actual compression step.

Preferably the tablets conforming to the invention are used to produce pharmaceutical forms capable of releasing the oxycodone they contain over a period of 24 hours, making it possible to administer the oxycodone in a once-a-day formulation.

Under the present invention, the terms deliberate misuse or drug abuse are used to designate any intentional deterioration of pharmaceutical forms. In particular, the notion of drug abuse concerns reducing the tablets to powder, then inhaling this powder or dissolving it in a small quantity of liquid for its parenteral injection.

The term matrix tablet is used to designate a tablet whose inner structure is homogeneous and identical from the core towards the periphery of the tablet. Therefore the tablets of the present invention consist of a homogeneous mixture of oxycodone in powder or granule form and of a compression matrix containing at least one excipient chosen from the group comprising sustained-release, water-insoluble, pH-independent polymers, mineral excipients and their mixtures.

Under the present invention, the term compression matrix is used to designate all the excipients which take part in the cohesion of the tablet. Said compression matrix is both water-insoluble and has a certain permeability (hydrophilic matrix) or a porous network (inert matrix) responsible for gradual release of the active ingredient, which does not vary in relation to the pH conditions of the medium.

The term « compression mixture » in the present application is used to designate all the constituents of the tablet (oxycodone, whether granulated or not, and the constituents of the compression matrix) before their compression into tablet form.

In the present application, the notions of crush resistance and of hardness are both used to characterize the tablets. Hardness characterizes the tensile strength of the tablet under a diametral-compression test. A round tablet is placed between two jaws, one of which is fixed and the other mobile. Hardness corresponds to the force applied by the mobile jaw which causes rupture of the tablet into two more or less equal parts. It is expressed in Newtons (N) or Kilonewtons (kN) (see European Pharmacopoeia: ref: 01/2005:20908).

Crush resistance is inferred from measurement of hardness: it is a parameter which takes into account the surface area of the tablet exposed to the force, and corresponds to strength per unit surface area expressed in Pascals (Pa) or Megapascals (MPa), 1 MPa corresponding to 1 Newton per mm$^2$. Crush resistance is a parameter of particular interest to compare the behaviour of tablets with different surface areas, since it does not require recourse to the parameter of tablet size. Its calculation formula is the following (as per « Determination of tablet strength by the diametral-compression test ». Fell, J. T.; Newton, J. M. J. Pharm. Sci., 59 (5): 688-691 (1970)):

$$Rd = \frac{2 \times F}{\pi \times D \times h}$$

in which:
Rd is the diametral tablet breaking load (in MPa)
F is the hardness of the tablet (in N)
D is the diameter of the tablet (in mm)
H is the thickness of the tablet (in mm).

In the present application, the expression « sustained-release » polymers is used to designate polymers routinely used in the pharmaceutical industry to control the release of an active ingredient into its dissolution medium. In the present application, the sustained-release polymers used are water-insoluble, which means that release of the active ingredient into the surrounding medium occurs exclusively via a phenomenon of simple diffusion, with no erosion or gradual disintegration of the polymer. These polymers effectively have certain permeability vis-à-vis the surrounding medium, responsible for gradual diffusion of the active ingredient out of the polymer matrix. Therefore the lower the permeability of the polymer, the more the diffusion of the active ingredient is sustained.

Under the present invention, the expression pH-independent polymers is used to designate those polymers capable of forming a permeable network or matrix, and whose permeability is not influenced by the pH of the surrounding medium.

Under the present invention, the expression pharmaceutically acceptable salts of oxycodone is used to designate salts which are pharmaceutically equivalent to the base, in particular oxycodone sulphate, oxycodone hydrochloride, oxycodone trifluoroacetate, oxycodone thiosemicarbazone hydrochloride, oxycodone pentafluoropropionate, p-nitrophenylhydrazone oxycodone, o-methyloxine oxycodone, thiosemicarbazone oxycodone, semicarbazone oxycodone, phenylhydrazone oxycodone, hydrazone oxycodone, oxycodone hydrobromide, oxycodone mucate, oxycodone methylbromide, oxycodone oleate, n-oxide oxycodone, oxycodone acetate, dibasic oxycodone phosphate, oxycodone, monobasic oxycodone phosphate, inorganic or organic salts of oxycodone, oxycodone acetatetrihydrate, oxycodone bis (heptafluorobutyrate), oxycodone bis(methylcarbamate), oxycodone bis (pentafluoropropionate), oxycodone bis (pyridine-3-carboxylate), oxycodone bis (trifluoroacetate), oxycodone bitartrate, oxycodone chlorohydrate and oxycodone pentahydrate sulfate.

The tablets of the invention are tablets with very high hardness (hereunder called « ultra-hard tablets »). Their structure is such that their crushing cannot be envisaged using conventional domestic techniques, and their dissolution in an aqueous medium, even an acidified medium, is practically impossible.

This extreme hardness is also accompanied by little or no friability, which means that these tablets are a pharmaceutical form of choice for oxycodone which can be given drug abuse. This very low or non-friability makes the tablets practically unbreakable using conventional or domestic techniques (spoon, mortar, lighter . . . ).

The tablets of the invention are also practically insoluble in an aqueous medium, even at low pH (pH<3). These characteristics make them difficult to administer via parenteral route.

The tablets of the invention are also insoluble in an alcohol medium, which means that they can be taken even if alcohol is ingested, thereby avoiding accidental misuse.

Additionally, the tablets of the invention, despite their extremely hard, resistant outer structure, allow sustained release of the oxycodone contained in said matrix. The tablets of the invention therefore allow release of oxycodone into the body over a period that is greater than 8 hours, preferably greater than 12 hours, further preferably greater than 20 hours.

Advantageously, the tablets of the invention are used to produce pharmaceutical forms containing oxycodone to be taken once-a-day.

Finally the matrix structure of the tablet according to the invention, consisting of a mixture of known sustained-release excipients approved for oral use and of granules containing the active ingredient, is extremely simple, allowing for its easy industrial production since it requires a simple compression step of the mixture without the need to heat the compression tooling and/or mixture to be compressed either before or during the actual compression step.

Advantageously, the compression matrix of the tablets conforming to the invention represents 50 to 98 weight % of the total weight of the tablets, further advantageously 85 and 95 weight % of the total weight of the said tablets.

The excipients, which can be used alone or in a mixture in the matrix composition of the tablets of the invention, can be of organic type; they then belong to the group comprising cellulose derivatives and in particular microcrystalline cellulose (e.g. that sold under the trade name Avicel®) and ethylcellulose (e.g. that sold under the trade name Aqualon®), the polymers of the family of water-insoluble, pH-independent methacrylic acids, in particular the grades Eudragit® RL 12.5, RL PO & RL 100 and RS 12.5, RS PO and RS 100, the derivatives of polyvinylalcohols, the polymers of lactic and glycolic acids (PLGA), starches, waxes, derivatives of polyvinyl acetates, derivatives of polyvinylpyrrolidone and mixtures of polymers such as the mixture of microcrystalline cellulose and [polyvinyl acetate/polyvinylpyrrolidone (80:20)] (sold under the trade name Kollidon SR®) and the mixture of microcrystalline cellulose and [poly(ethylacrylate/methylmethacrylate/trimethylamonioethyl methacrylate chloride) (1:2:0.2)].

Advantageously, the sustained-release, water-insoluble, pH-independent polymers of the present invention belong to the group comprising cellulose derivatives, the mixture of microcrystalline cellulose and [polyvinyl acetate/polyvinylpyrrolidone (80:20)] (sold under the trade name Kollidon SR®) and the mixture of microcrystalline cellulose and [poly(ethylacrylate/methylmethacrylate/trimethylamonioethyl methacrylate chloride) (1:2:0.2)].

The excipients of the compression matrix can also be of mineral type: they then belong to the group comprising calcium phosphates (in particular dicalcium or tricalcium phosphates), aluminium and silicon silicates, and magnesium carbonates.

The compression matrix of the tablets according to the invention can advantageously consist of a mixture of several of the above-mentioned excipients. It may be a mixture of organic polymers such as microcrystalline cellulose and of vinyl derivatives in variable proportions, or a mixture of organic polymer+mineral derivative such as a mixture of calcium and silicon silicate+microcrystalline cellulose in variable proportions.

The excipients present in the compression matrix of the tablets conforming to the present invention advantageously represent between 40 and 100 weight % of the total weight of said matrix, advantageously 50 to 90 weight % of the total weight of the matrix.

According to one advantageous embodiment of the invention, the compression matrix consists of a (1:1) mixture of two polymers, advantageously it consists of a (1:1) mixture of microcrystalline cellulose and of the mixture [polyvinyl acetate/polyvinylpyrrolidone to a proportion of 80:20 (sold under the trade name Kollidon SR®)], or a mixture of microcrystalline cellulose and [polyethylacrylate/methylmethacrylate/trimethyl-amonioethyl methacrylate chloride in proportions of (1:2:0.2)]. Advantageously, these two polymers each represent a weight proportion in the order of 40% of the total weight of said compression matrix.

The compression matrix can advantageously, in addition to the excipients of the compression matrix, contain one or more excipients intended to promote the conducting of the compression process such as anti-adherent agents e.g. colloidal silica, talc, magnesium stearate, Polyethylene Glycol (PEG) or calcium stearate, or to promote cohesion of the tablets on compressing such as binders conventionally used for this purpose, in particular starches, cellulose derivatives, or fillers, lubricants, plasticizers, bulking agents, or sweeteners or colouring agents.

If present, these excipients are used conventionally to the proportion of 0.1 to 10 weight % of the total weight of the compression matrix, preferably between 0.5 and 5 weight %.

Said compression matrix may also comprise at least one the following substances (a) to (f) or a mixture thereof:
  (a) a substance which irritates the nasal and/or pharyngeal tracts,
  (b) an agent increasing viscosity, allowing the formation of a gel when the tablet is dissolved in a minimum amount of water,
  (c) an antagonist of oxycodone,
  (d) an emetic substance,
  (e) a colouring agent as aversive agent,
  (f) a bittering substance.

The antagonist (c) is advantageously chosen from the group comprising naloxone, naltrexone, nalmefene, nalid, nalmexone, nalorphine and naluphine, these different compounds each being either in a pharmaceutically acceptable form, in particular a base or salt, or a solvated form. These antagonists are present in doses conventionally used, in particular to the proportion of 0.1 to 100 mg per tablet.

In one advantageous embodiment of the invention, said antagonist agent is naloxone or one of its pharmaceutically acceptable salts.

The tablets conforming to the invention are therefore of particular interest as reservoirs for oxycodone, an active ingredient which may be the subject of drug abuse and intended to be released into the body over periods of more than 8 hours, preferably more than 12 hours, and further preferably more than 20 hours.

The oxycodone contained in the tablets of the invention can be present in any form known to those skilled in the art, in particular in powder, crystal or granule form.

Preferably, the tablets of the invention are used to produce once-a-day pharmaceutical dosage forms.

The oxycodone contained in the tablets of the invention can represent between 5 and 70 weight % of the total weight of the tablet. Advantageously the oxycodone represent 10 to 50 weight % of the total weight of the tablet. It can be added directly to the mixture to be compressed, coated on carriers (to obtain microgranules) or wet- or dry-granulated (to obtain granules).

If the oxycodone is in the form of microgranules, these microgranules can be obtained conventionally by depositing (coating) the active ingredient(s) on the surface of pharmaceutically neutral carriers, such as pre-manufactured microspheres containing cellulose or a mixture of sugar and starch sold under the name "neutral cores" or "sugar spheres", or they may be granules of other excipients such as lactose for example.

The depositing (coating) method of the active ingredient is a conventional method known to those skilled in the art. Therefore depositing (coating) can be made by spraying a solution or suspension of oxycodone onto the surface of the neutral carrier, or by spraying the oxycodone in powder form onto the surface of the carrier previously moistened with a binder solution.

The granules of oxycodone may also be obtained by dry or wet granulation of the active ingredients of interest, generally in the presence of at least one binding agent and optionally a wetting agent, depending on techniques, here again well known to those skilled in the art.

The granules thus obtained are mixed with the excipients of the compression matrix, and the mixture is then compressed.

The exceptional hardness of the tablets conforming to the invention can be obtained without it being necessary to apply a heating step, before or during compression, either to the mixture to be compressed (compression matrix and oxycodone) and/or to the compression tooling (press).

Advantageously, the granules have a diameter allowing a good compression yield, i.e. generally between 100 and 600 μm.

According to another embodiment of the invention, and if particle size so permits, the oxycodone is mixed directly with the excipients forming the compression matrix, then the mixture is directly compressed.

Finally, another possible embodiment of the invention consists of mixing the oxycodone with the excipient(s) of the compression matrix, then dry- or wet-granulating this mixture to obtain directly compressible granules.

The tablets conforming to the invention can be of any shape and size allowing tablets of high hardness to be obtained. Advantageously the total surface area of the tablet is less than 150 mm².

The present invention is therefore suitable for the production of tablets with either low or high doses of active ingredient.

According to one particular embodiment of the invention, the tablets can be film-coated with an outer coating which those skilled in the art will know how to adapt in relation to needs and the intended function of this coating.

For example, the outer coating can be applied for the purpose of protecting the active ingredient, if it is a labile active ingredient sensitive to the low pH values of the gastric medium for example, in which case the term gastroresistant coating is used.

Also, the outer coating can be applied to further delay diffusion of the active ingredient through the matrix. For this purpose different grades of ethylcellulose can be used, or of methacrylic polymers well known to the skilled person.

Finally, the outer coating can be used to modify the cosmetic appearance of the tablet (texture, colour) and/or palatability (taste/feel in the mouth) for the patient. In particular, excipients can advantageously be used such as cellulose derivatives or acrylic derivatives well known to those skilled in the art, to mask the taste of the active ingredient if necessary.

Said coating can therefore consist of a mixture of one or more excipients of different type known to those skilled in the art, used either alone or in a mixture for the different functions listed above.

The excipient(s) used for coating are applied in a manner known to those skilled in the art, in the necessary quantity to obtain the desired function(s).

These excipients can be applied to the surface of the tablet in conventional manner by spraying a solution or suspension of coating agent in a solvent, in a perforated pan or fluidised bed for example.

The present invention also concerns the method to manufacture the tablets of the invention. This method comprises the following steps:
- mixing the oxycodone with the excipient(s) of the compression matrix,
- optional granulation, and
- compressing said mixture under conditions chosen so that said tablet has a crush resistance of at least 4 MPa, advantageously at least 6 MPa,
- optional coating of the tablet.

If the coating polymer of the tablet is a sustained-release polymer, the coated tablets conforming to the invention can advantageously undergo a curing step of said coating polymer to guarantee its physical and chemical stability. This step is conducted under controlled temperature conditions, below the melt temperature of the active ingredient, and for a controlled time which is dependent upon the coating polymer and which may last between 1 minute and several months, with a relative humidity rate of 50 to 99%. This step can be conducted in an oven or pan.

The active ingredient can be mixed directly in the compression matrix, or mixed in the form of previously prepared granules or microgranules. This granulation step improves the uniform resistance of the tablets produced. Preferably, for granules, wet-granulation is used (aqueous or organic), or for microgranules the active ingredient is deposited by spray-coating in solution or suspension onto neutral carriers.

Compression is performed on a rotary compressing machine with pre-compression station. The compression parameters must be chosen so that the hardness of the tablets obtained is adapted to the present invention. However, it is not necessary to apply any heating step either before and/or during compression to the mixture to be compressed or to the compression tooling, for the purpose of achieving the exceptional hardness observed with the tablets of the invention. The applied compression forces lie between 10 kN and 160 kN, advantageously between 30 kN and 80 kN. They are chosen to be compatible with the punch material and so that they can be used at industrial production rates, whilst allowing tablets to be obtained whose tensile strength is greater than 4 MPa, and preferably greater than 6 MPa.

Examples 1 to 10 and FIGS. 1 to 14 given below are intended to illustrate the invention but do not in any way limit its scope.

FIG. 1 gives the dissolution profile in phosphate buffer medium pH 6.8 (monopotassium phosphate/disodium phosphate) of 40 mg oxycodone HCl tablets, non-film coated, obtained according to example 1.

FIG. 2 gives the dissolution profile at pH 6.8 of non-film coated, 40 mg oxycodone HCl tablets, obtained according to example 2.

FIG. 3 gives the dissolution profile at pH 6.8 of tablets conforming to example 2, film-coated with a layer of ethylcellulose EC30 D, which have undergone curing under the conditions of example 3.

FIG. 4 gives the comparative dissolution profiles of oxycodone matrix tablets according to the invention in an ethanol-free 0.1 N HCl medium, and in a 0.1 N HCl medium containing 40% ethanol such as measured according to example 4.

FIG. 5 illustrates the dissolution profiles of oxycodone matrix tablets conforming to the invention in two dissolution media of different pH (1.2 and 6.8) following the operating mode described in example 4.

FIG. 6 illustrates the 24-hour dissolution profiles of 40 mg oxycodone tablets conforming to the invention, after a storage period in alu/alu blister packs under accelerated stability conditions of 1 month, 2 months, 3 months and 6 months under the conditions of example 4.

FIG. 7 illustrates the 24-hour dissolution profiles of 20 mg oxycodone tablets conforming to the invention, after a storage period in HDPE bottles with a desiccant under conditions of accelerated stability of 1 month, 2 months and 3 months.

FIG. 8 gives the plasma profiles of oxycodone after once-a-day administering of 40 mg oxycodone tablets conforming to the invention, and 40 mg oxycodone tablets of the reference product OxyContin®, according to example 4.

EXAMPLE 1

Figure 1:
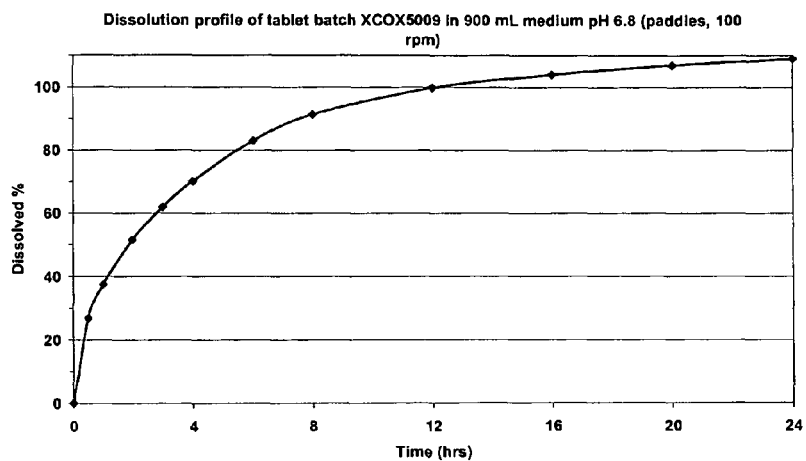

Manufacture of Tablets Containing Granules Obtained by Granulating Oxycodone HCl and 4.87% HPMC and Containing a Compression Matrix Consisting of a (1:1) Mixture of Two Excipients [Microcrystalline Cellulose and (PVA/Povidone 80:20)]

1. Preparation of the Tablets
1.1. Preparation of Oxycodone Granules

The granules are obtained by wet granulation of the active ingredient (oxycodone HCl, batch NO DV000165; McFarlan Smith, England) and hydroxypropylmethylcellulose (HPMC) grade Pharmacoat® 606, Brenntag) acting as binder. Granulation is conducted in a fluidised bed (GCPG-1, Würster, Glatt, Germany) by bottom-spraying a solution of the binder (HPMC) onto the powdered active ingredient.

Oxycodone is added to the fluidised bed and placed in sustentation. The binder solution is sprayed onto the powder which aggregates to form granules. Water is progressively removed by evaporation and after a final drying step. The final drying step in an oven (16 hours at 60° C.) is conducted to obtain an acceptable final water content (less than 6%).

The proportions of HPMC and oxycodone are given in Table 1.

TABLE 1

| Ingredients | Percentage [%] | Batch n° of granules XOXY4979 Wt. in grams/batch |
|---|---|---|
| Oxycodone HCl | 95.13 | 500.0 |
| HPMC (Pharmacoat® 606) | 4.87 | 25.6 |
| Purified water | — | 336.9 |
| Total (dry) | 100.0 | 525.6 |

The parameters for the granulation process are given in Table 2; phase 1 corresponds to spraying of the first 175 g of solution, phase 2 corresponds to spraying of the remaining 185 g:

TABLE 2

| Step | Batch n° of granules XOXY4979 | |
|---|---|---|
| | 1 | 2 |
| Input temperature (° C.) | 40 | 45 |
| Output temperature (° C.) | 23-29 | 24-27 |
| Product temperature (° C.) | 21-28 | 25-27 |
| Spray pressure (bar) | 1.0 | 1.2 |
| Spray rate (g/min) | 10.0 | 6.0 |
| Drying step (oven) | 16 hours at 60° C. | |

The granules obtained after the fluidised bed step have the characteristics indicated in Table 3.

TABLE 3

| Batch number | Mean particle size (µm) | Apparent density g/mL | Flow time (Sec./100 g) | Relative humidity (%) |
|---|---|---|---|---|
| XOXY4979 (4.87% HPMC) | 108.7 | 0.450 | 6 | 3.47 |

1.2. Preparation of the Compression Matrix

A pre-mixture of microcrystalline cellulose (Avicel™ PH102, FMC) and precipitated silica (Syloïd® 244, Keyser & Mc Kay) is formed in a cubic mixer (AR 401, Erweka) for 2 min at 40 rpm. The mixture of polyvinylacetate/povidone (80:20) (Kollidon® SR, BASF) and the oxycodone granules prepared as described under step 1.1 are added to the pre-mixture and homogenisation is conducted in the cubic mixer for 15 minutes at 40 rpm. Finally, the lubricant (magnesium stearate, Quimdis) intended to limit sticking and friction during compression is added to the preceding mixture using the mixing parameters: 5 minutes at 40 rpm.

The quantity of oxycodone granules used is determined with a view to producing tablets containing 40 mg oxycodone.

The proportions of each of the excipients are summarized in Table 4.

TABLE 4

| | Batch number XCOX5009 | |
|---|---|---|
| Ingredients | Percentage [%] | Weight (mg/tablet) |
| Oxycodone granules (lotXOXY4979) | 19.83 | 44.62 |
| Kollidon® SR | 39.74 | 89.40 |
| Avicel® PH102 | 39.73 | 89.40 |
| Syloid® 244 | 0.20 | 0.45 |
| Magnesium stearate | 0.50 | 1.13 |
| Total | 100.00 | 225.00 |

1.3. Compression

The compression step of the final mixture obtained in the preceding step is conducted on a compression press (PR-12, Sviac) with a compression force of 35 kN using oblong punches 11 mm×5 mm. Compression is conducted conventionally, without the mixture to be compressed or the compression tools being subjected to a heating step either before or during the actual compression step.

The characteristics of the tablets obtained are summarized in Table 5. The mean values correspond to the mean calculated for 20 tablets.

TABLE 5

| Batch n° of tablets | XCOX5009 |
|---|---|
| Weight (mg) | 225 |
| Shape | oblong |
| Size (mm) | 11 × 5 |
| Thickness (mm) | 4.15 |
| Hardness (N) | 381 |
| Crush resistance (MPa) | 6 |
| Friability (%) | 0.0 |

The tablets obtained following Example 1 have very high crush resistance, 6 Mpa, and zero friability, without there being any need to heat the matrix constituents or the compression press before or during compression.

1.4. Dissolution Profile of the Tablets Obtained According to Example 1

The tablets obtained according to Example 1 have hardness and friability characteristics which make them practically unbreakable, meaning that they are excellent candidates for a pharmaceutical medium which can limit abuse thereof by crushing.

Additionally, the applicant has evidenced that these tablets are practically insoluble in an aqueous medium, even if acid: on completion of the dissolution tests (over 24 h) the tablets remain intact at the bottom of the dissolution vessel, both in a pH 6.8 buffered medium, and in a pH 1.2 acid medium.

2. Dissolution Method

Measurement of the dissolution of the tablets obtained in Example 1 is performed in 900 mL of phosphate buffer, pH 6.8 (monopotassium phosphate/disodium phosphate) using the rotating paddle method with a paddle rotating speed of 100 rpm (Type II paddle apparatus in accordance with the American Pharmacopoeia USP 24).

The dissolution medium is continuously analysed by chromatography (HPLC) with UV detection. For each sample, measurement is performed on at least three vessels.

The results of the dissolution tests are summarized in FIG. 1.

Unexpectedly, it is observed that the tablets of the invention, even though they are insoluble, nevertheless have the capacity to release the active ingredient they contain over an extended period, i.e. over periods of more than 8 hours, preferably more than 12 hours, and further preferably more than 20 hours.

Said tablets are therefore of particular interest for the production of pharmaceutical forms of « Once-a-Day» type, i.e. only requiring one administering per day.

EXAMPLE 2

Manufacture of Tablets Containing Granules Obtained by Granulating Oxycodone and 6.46% HPMC and Containing a Compression Matrix Consisting of a (1:1) Mixture of Two Excipients (Microcrystalline Cellulose and PVA/Povidone 80:20)

In this example, the applicant sought to determine the influence of the quantity of binder used during the granulation step on the dissolution profile of the tablets.

The granulation step is identical to the step described to produce tablets conforming to Example 1, with the sole exception that this time the quantity of binder (HPMC, Pharmacoat® 606) is 6.46 weight % of the total weight of the granules. The composition of these granules is summarized in Table 6.

TABLE 6

| Ingredients | Tablet batch n° XOXY5103 | |
|---|---|---|
| | Percentage [%] | Weight (g/batch) |
| Oxycodone HCl | 93.54 | 590.5 |
| HPMC (Pharmacoat ® 606) | 6.46 | 40.8 |
| Purified water | — | 483.9 |
| Total (dry) | 100.0 | 631.3 |

The mixing and compression steps are then conducted following exactly the same parameters as in Example 1, using the same qualitative and quantitative formula.

The characteristics of the tablets obtained according to Example 2 are summarized in Table 7. The mean values correspond to the mean calculated per 10 or 20 tablets.

TABLE 7

| Batch n° of tablets | XCOX5111 |
|---|---|
| Weight (mg) | 227.0 |
| Shape | Oblong |
| Size (mm) | 11 × 5 |
| Thickness (mm) | 4.2 |
| Hardness (Newtons) | 397 |
| Crush resistance (MPa) | 6 |
| Friability (%) | 0.0 |

The tablets obtained following Example 2 show very strong crush resistance, equal to 6 Mpa, and zero friability. No heating step before or during compression was necessary to obtain tablets of such hardness.

Figure 2:
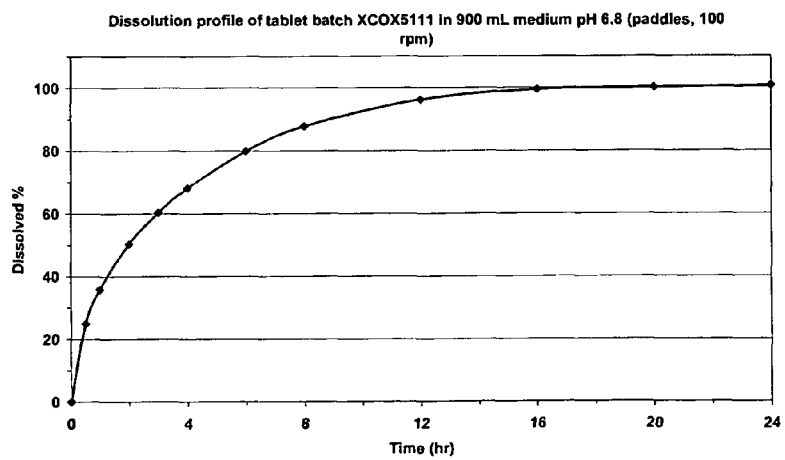

The dissolution profile of these tablets is then determined as described in Example 1. This profile is illustrated FIG. 2.

The quantity of binder used has little influence on the release kinetics which extend over 24 h.

EXAMPLE 3

Tablets Obtained According to Example 2, Film-Coated with an Outer Coating of Aquacoat® ECD-30 (Ethylcellulose)

In this example, an assessment is made of the influence of an outer coating applied to the oxycodone tablets obtained following Example 2. Here again, no heating step was applied either to the mixture to be compressed or to the compression tooling, whether before or during the actual compression.

1. Preparation of the Tablets 1.1. Sub-Coating

Prior to coating with the actual polymer, a sub-coating step is applied to the tablets obtained in Example 2.

This sub-coat is intended to improve the surface condition of the tablets. It consists of a mixture of HPMC (Pharmacoat® 603), an anti-foaming agent (Simethicone, Dow Corning), a lubricant (micronised talc, Luzenac (Univar) and anti-static agent (Syloid 244, Keyser & McKay), the HPMC representing a weight gain of 3% relative to the total weight of the uncoated tablets. The proportions of each of the excipients are given in Table 8.

TABLE 8

| | Batch n° of tablets XCOX5112.1 | | |
|---|---|---|---|
| Ingredients | Percentage [%] | Weight/pan (g) | Weight (mg/tablet) |
| Tablets XCOX5111 | 95.96 | 1000.0 | 227.00 |
| HPMC (603) | 2.88 | 30.0 | 6.81 |
| Simethicone (dry weight) | 0.01 | 0.1 | 0.02 |
| Talc | 0.86 | 9.0 | 2.03 |
| Syloid ® 244 | 0.29 | 3.0 | 0.69 |
| Purifd. water** | N/A | 308.5 | N/A |
| Total (dry) | 100.00 | 1042.07 | 234.5 |

**Note: the water is removed during the process;
N/A: Not Applicable

This sub-coating is performed in conventional manner in a perforated pan (Trislot).

The parameters for the coating process are summarized in Table 9.

TABLE 9

| Batch n° of tablets | XOXY5112.1 |
|---|---|
| Input temperature (° C.) | 38 |
| Output temperature (° C.) | 32 |
| Pan rotation speed(rpm) | 15 |
| Air flow rate (m³/h) | 150 |
| Spray pressure (MPa) | 0.12 |
| Spray rate (g/min) | 2.0-2.6 |

1.2. Coating

The actual coating of the previously sub-coated tablets is performed in a perforated pan (Trislot).

Coating is conducted using an aqueous dispersion of ethylcellulose (Aquacoat® ECD-30, FMC) the proportion of ethylcellulose representing 2.87 weight % of the total weight of the coated tablets. The proportion of the different excipients is given in Table 10. Here again, no specific heating step of the tablets was performed, either before or during application of the sub-coat or the actual coating.

TABLE 10

| Ingredients | Batch n° of tablets XCOX5112.2 | |
|---|---|---|
| | Percentage [%] | weight/pan (g) |
| Tablets of batch XCOX5112.1 | 95.75 | 1042.09 |
| Aquacoat ® ECD-30 (sec) | 2.87 | 31.24 |
| Dibutyl sebacate | 0.69 | 7.51 |
| Talc | 0.52 | 5.66 |
| Syloïd ® 244 | 0.17 | 1.85 |
| Purified water** | N/A | 185.04 |
| Total (dry) | 100.00 | 1088.35 |

**Note:
the water is removed during the process; N/A: Not Applicable

The parameters of the coating process are reproduced in Table 11.

TABLE 11

| Batch n° of tablets | XCOX5112.2 |
|---|---|
| Input temperature (° C.) | 40 |
| Output temperature (° C.) | 34 |
| Pan rotation speed (rpm) | 15 |
| Air flow rate (m³/h) | 140 |
| Spray pressure (MPa) | 0.12 |
| Spray rate (g/min) | 1.5-2.0 |
| Curing step | XCOX4976.2 |
| Input temperature (° C.) | 75 |
| Output temperature (° C.) | 65 |
| Product temperature (° C.) | 60 |
| Pan rotation speed (rpm) | 3 |
| Air flow rate (m³/h) | 140 |
| Time (hours) | 24 |

1.3. Curing Step

This is conducted in a perforated pan after coating, for 24 hours at 60° C. to allow stabilization of the film coating.

The tablets undergo an extended curing step (3 months) at 40° C. and 75% humidity to increase their hardness and to prevent their crushing by conventional techniques (under a lighter or spoon) but also by less conventional but more efficient techniques (mortar, pliers or hammer for example).

Figure 3:
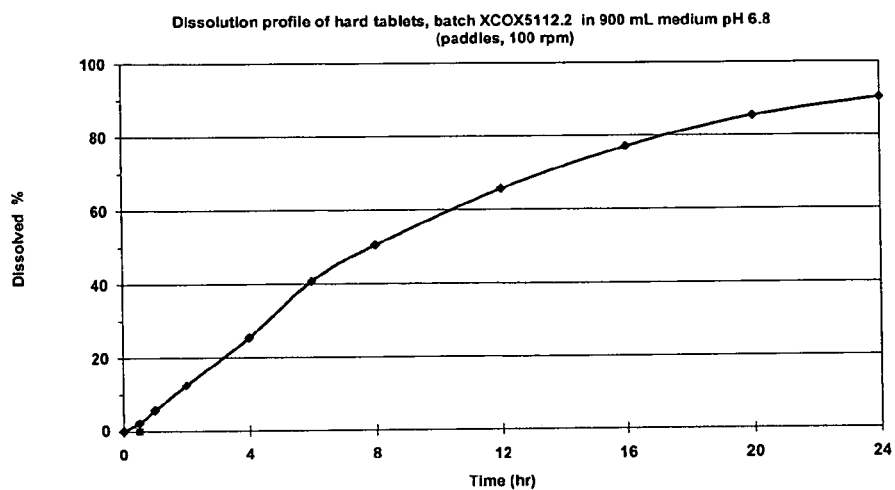

The tablets thus hardened have a hardness greater than 500 N, which is equivalent to a crush resistance of more than 7.4 MPa. Under these conditions, release of the active ingredient is maintained with more than 90% of active ingredient released over 24 h as illustrated FIG. 3.

EXAMPLE 4

Coated Alcohol-resistant and pH-independent Oxycodone Tablets

Coated, sustained-release, 40 mg oxycodone tablets are prepared (technical batch n° XCOX5111).

As in Example 1, the oxycodone is first granulated in a fluidised air bed (GPCG1) in the presence of water and a binding agent (HPMC 606).

4.1. Preparation of the Tablets

4.1.1. Preparation of the Compression Matrix

A pre-mixture of microcrystalline cellulose (Avicel® PH102, FMC) and precipitated silica (Syloïd® 244, Keyser & Mc Kay) is formed in a cubic mixer (AR 401, Erweka) for 2 min at 40 rpm. The polyvinylacetate/povidone mixture (80:20) (Kollidon® SR, BASF) and the oxycodone granules are added to the previous pre-mixture and homogenization is conducted in a cubic mixer for 15 minutes at 40 rpm. Finally, the lubricant (magnesium stearate, Quimdis) intended to limit adherence and compression friction is added to the previous mixture according to the mixing parameters: 3 minutes at 40 rpm.

The quantity of granules used is determined so as to manufacture tablets containing 40 mg oxycodone.

The proportions of each of the excipients are summarized in Table 12 below.

TABLE 12

| | | Batch number XCOX5111 | |
|---|---|---|---|
| Ingredients | Function | Percentage [%] | Weight (mg/tablet) |
| Oxycodone HCl granules | Granulated active ingred. | 20.25 | 45.56 |
| Kollidon ® SR | Sustained-release agent | 39.53 | 88.93 |
| Avicel ® PH102 | Sustained-release agent | 39.53 | 88.93 |
| Syloïd ® 244 | Flow agent | 0.20 | 0.45 |
| Magnesium stearate | Lubricant | 0.50 | 1.13 |
| Total | | 100.00 | 225.00 |

4.1.2. Compression

The compression step of the final mixture obtained in the preceding step is conducted on a compression press (PR-12, Sviac) under a compression force of 35 kN using oblong punches whose sizes are given in the table below.

Compression is performed in conventional manner without either the mixture to be compressed or the compression tooling being subjected to a heating step, whether before or during the actual compression step.

The tablets containing 40 mg oxycodone obtained after this step have the following characteristics which are given in Table 13:

TABLE 13

| Batch n° of tablets | XCOX5111 |
|---|---|
| Weight (mg) | 225 |
| Size (mm) | 11 × 5 |
| Shape | oblong |
| Thickness (mm) | 4.2 |
| Surface area (mm²) | 55 |
| Hardness (N) | 350 |
| Crush resistance (MPa) | 5.2 |
| Friability (%) | 0.0 |

It is therefore ascertained that the tablets conforming to the invention have very high crush resistance, of more than 5 MPa.

Other tablets containing a dose of 20, 40 and 80 mg are produced using a different process: the oxycodone granules are prepared in a high shear granulator. The mixture to be compressed is prepared as described for Examples 1 and 2. The tablets are compressed on a SVIAC PR12 rotary compressor, using oblong punches of different sizes depending on the doses to be manufactured, under a compression force in the order of 10 to 15 kN.

Their physical characteristics are given in Table 14 below:

TABLE 14

| Dose | Tablet weight | Size L × W × Thickn. | Hardness (Crush resistance) |
|---|---|---|---|
| 20 mg | 175 mg | 11.0 × 5.0 × 3.8 mm | 300 N (4.9 MPa) |
| 40 mg | 225 mg | 11.0 × 5.0 × 4.2 mm | 350 N (5.2 MPa) |
| 80 mg | 325 mg | 13.0 × 6.0 × 4.5 mm | 400 N (5.6 MPa) |

The tablets thus manufactured all have excellent crush resistance, which is greater than 6 Mpa irrespective of their size, even though at no time during the process was it necessary to heat the constituents of the tablets or the compression tooling to increase their hardness and resistance.

The « bare » tablets containing 40 mg of active ingredient after the compression step are then coated with a coating intended to delay their release profile into the body.

4.1.3. Coating

Coating of the tablets is conducted in a perforated pan (Trislot).

Coating uses an aqueous dispersion of ethylcellulose (Aquacoat® ECD-30, FMC) the proportion of ethylcellulose representing 2.87 weight % of the total weight of the coated tablets.

A curing step of the coating film is carried out in an oven at 60° C. for 24 h.

The proportion of the different excipients and the general formula of the coated tablets obtained are given in Table 15 below.

TABLE 15

| | Batch n° XCOX5112 | |
|---|---|---|
| | Percentage | mg/tablet |
| Oxycodone (DV000165) | 17.40 | 42.98 |
| HPMC 606 | 1.20 | 2.97 |
| Kollidon SR ® | 36.32 | 89.73 |
| Avicel PH102 | 36.32 | 89.73 |
| Magnesium stearate | 0.46 | 1.13 |
| HPMC 603 | 2.76 | 6.81 |
| Simethicone 30% (vs) | 0.01 | 0.02 |
| Aquacoat ECD-30 (vs) | 2.87 | 7.08 |
| DBS | 0.69 | 1.70 |
| Micronised talc | 1.35 | 3.34 |
| Syloid 244FP | 0.63 | 1.57 |
| Total | 100.00 | 247.06 |

Other uncoated tablets containing doses of 20, 40, 80 and 160 mg are also coated following the method described above.

Their physical characteristics observed after coating are given in Table 16 below:

TABLE 16

| Dose | Tablet weight | Size L × W × Thickn. | Hardness (Crush resistance) |
|---|---|---|---|
| 20 mg | 175 mg | 11 × 5 × 3.8 mm | 440 N (7.3 MPa) |
| 40 mg | 225 mg | 11 × 5 × 4.2 mm | 500 N (7.4 MPa) |

TABLE 16-continued

| Dose | Tablet weight | Size L × W × Thickn. | Hardness (Crush resistance) |
|---|---|---|---|
| 80 mg | 325 mg | 13 × 6 × 4.5 mm | 570 N (6.5 MPa) |
| 160 mg | 575 mg | 15 × 7 × 5.8 mm | 800 N (6.3 MPa) |

The tablets thus manufactured all have excellent crush resistance, which is greater than 6 MPa irrespective of their size.

2. Dissolution Curves with and without the Presence of Alcohol in the Dissolution Medium Coated 40 mg tablets prepared according to Example 4.3 are tested in dissolution under two conditions:

a) 0.1 N HCl medium without ethanol
b) 0.1 N HCl medium with 40% ethanol

Les dissolution conditions are as follows: rotating paddle method, paddle rotating speed: 100 rpm, volume of medium: 900 mL, 1 tablet per vessel. The oxycodone is assayed by 225 nm UV spectrophotometry.

Figure 4:
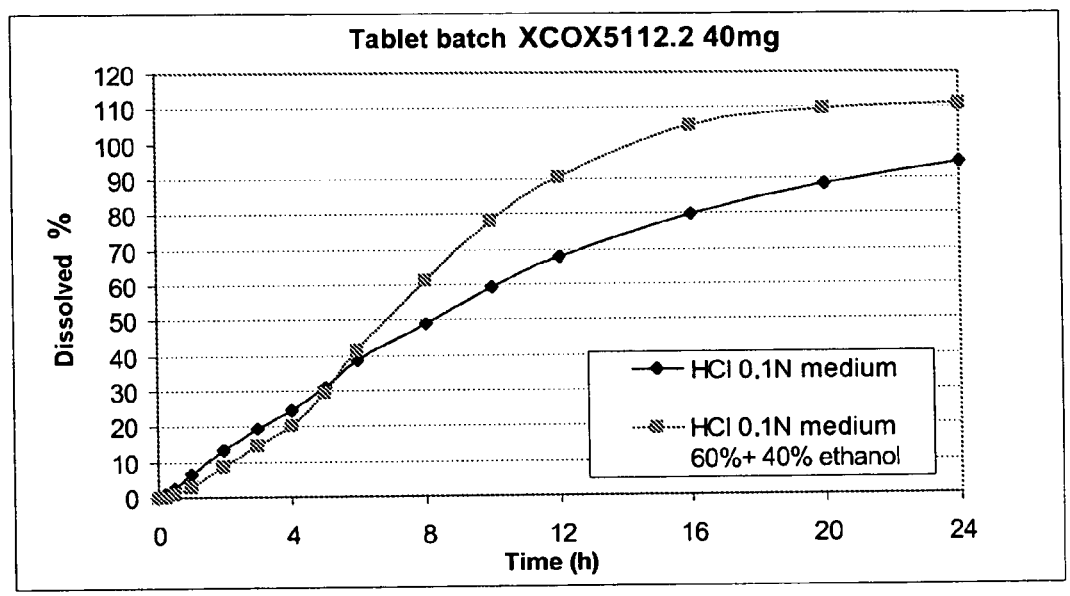

The results of the dissolution tests are given in FIG. 4.

It is found that, despite the presence of alcohol in the dissolution medium, the tablets of the invention maintain a sustained-release dissolution profile.

3. Dissolution Curves in Relation to pH 40 mg tablets prepared as described above in this example were also tested with respect to pH-independence i.e. their ability to maintain a constant release profile irrespective of the pH value of the dissolution medium.

Two experimental conditions were used:
Dissolution medium of pH 6.8
Dissolution medium of pH 1.2

Figure 5:
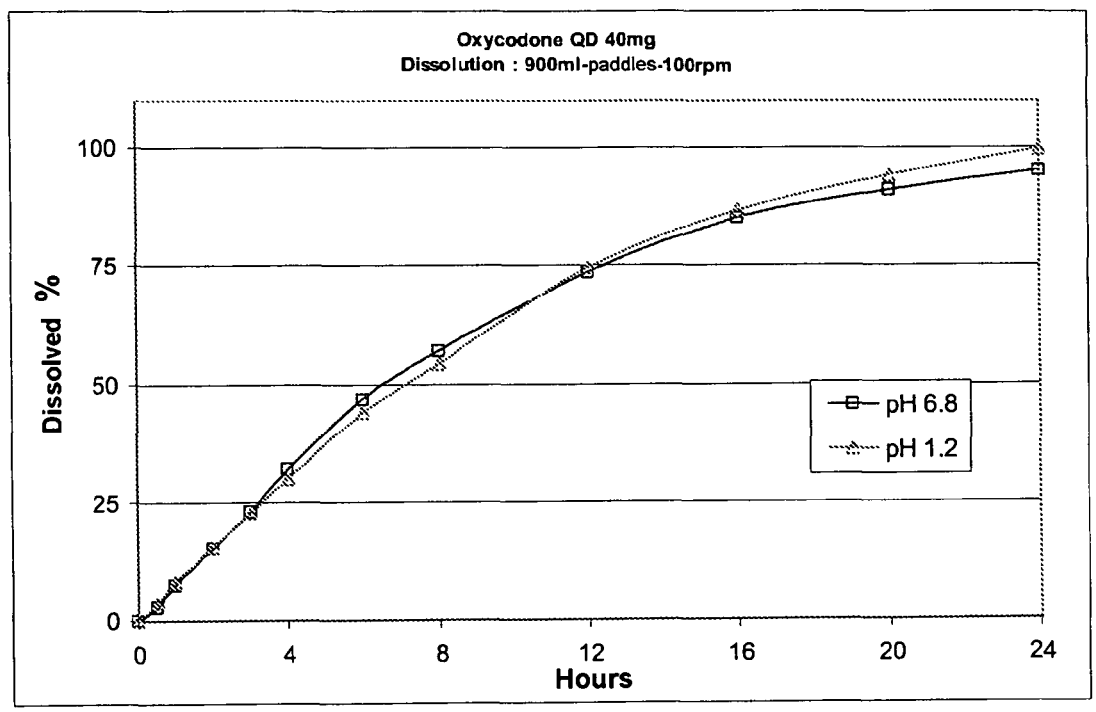

The dissolution profiles obtained are given in FIG. 5.

It is ascertained that irrespective of the acidity of the dissolution medium, the tablets conforming to the invention maintain a constant sustained-release profile.

These tablets can therefore be considered to be pH-independent, imparting thereto a particular advantage insofar as they can be used as vectors for any of type of active ingredient which is to be released over an extended time.

4.3. Stability Studies 4.3.1. Storage Stability

The coated tablets containing 40 mg oxycodone, obtained following the above-described method, are examined with regard to stability in order to determine their reaction to storage.

The tablets are stored for 6 months under accelerated stability conditions in accordance with ICH standards in force (45° C.; 75% humidity) in two types of packs: a) Al/Al aluminium blister pack, and b) HDPE bottles (high density polyethylene) in the presence of a desiccant.

The characteristics of the tablets after the storage period are summarized in Table 17 below:

TABLE 17

| Packaging | Initial dose | Dose after storage mg/tablet | Impurities | Hardness | Proportion of water |
|---|---|---|---|---|---|
| Blister Al/Al | 40 mg | 40.9 CV 0.5% | 0.17% | >500N | 3.5% |
| HDPE bottles | 20 mg | 19.9 CV 3.5% | 0.17% | 440N | 3.6% |

4.3.2. Dissolution Profiles Obtained after a Storage Period.

These dissolution profiles are obtained under the following conditions: rotating paddle method, paddle rotating speed: 100 rpm, volume of the dissolution medium: 900 mL, pH 6.8.

Figure 6:
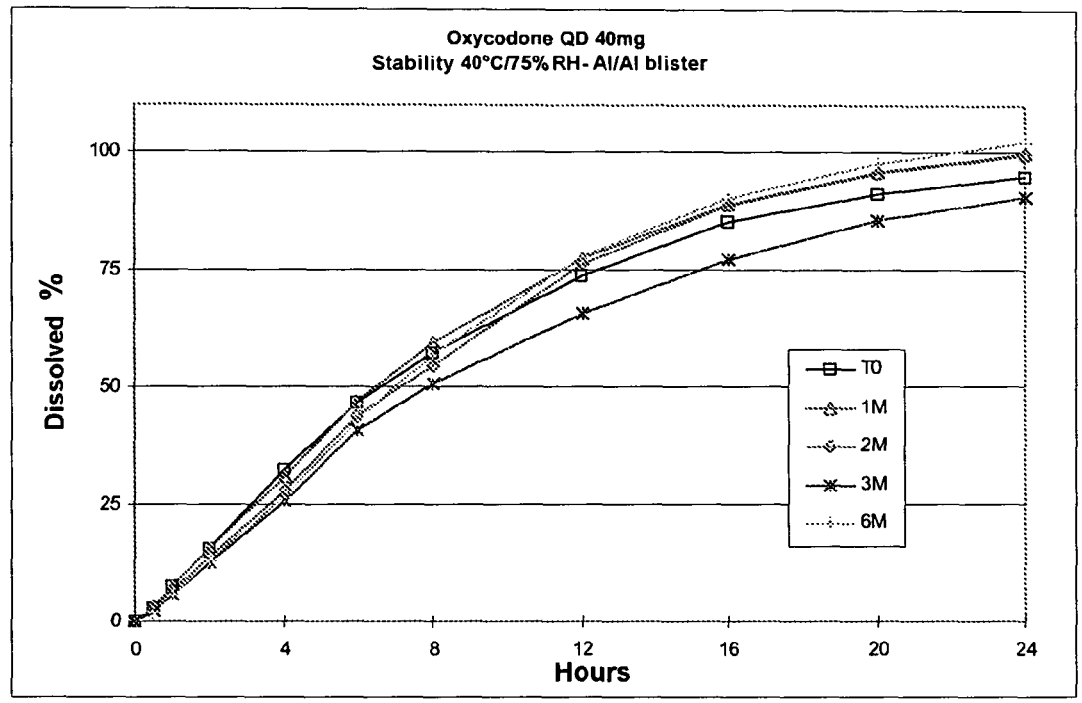
Figure 7:
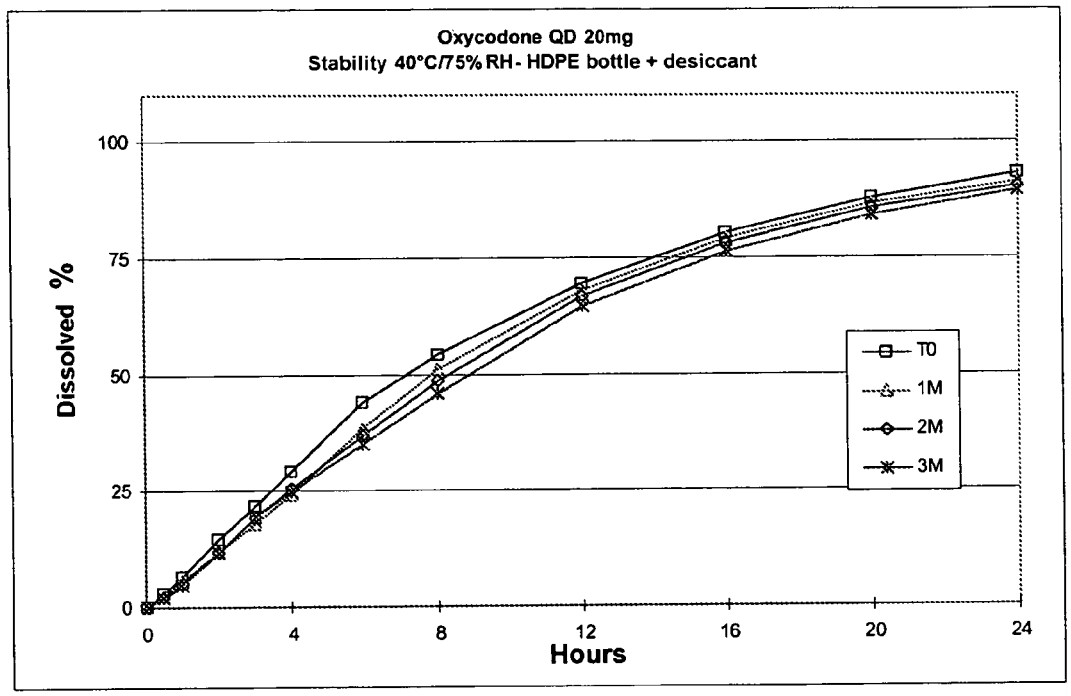

These are given in FIGS. 6 and 7.

It is found that not only is the quantity of active ingredient maintained over time, but also that the release profiles of the active ingredient and the extreme hardness of the tablets are maintained after a storage period of 6 months.

The tablets conforming to the invention are therefore stable and show a dissolution profile which is both pH-independent and independent of the presence (even strong presence) of alcohol in the dissolution medium.

4.4. Clinical Trials

The 40 mg tablets prepared in this example are also tested in vivo to determine the plasma profile of oxycodone in patients receiving said tablets.

A clinical trial (Algorithme, Canada, n° OXY/24018/001) was conducted in 12 healthy, fasting, male and female volunteers separated into two semi-groups. Each semi-group was successively given the two treatments (tablets of the invention and reference product) after an intermediate period without any treatment (wash-out period).

The reference product used in this trial was OxyContin®, a sustained-release oxycodone tablet taken twice a day, also containing a dose of 40 mg. (batch N° 121777, expiry date April 2007, Purdue).

Figure 8:
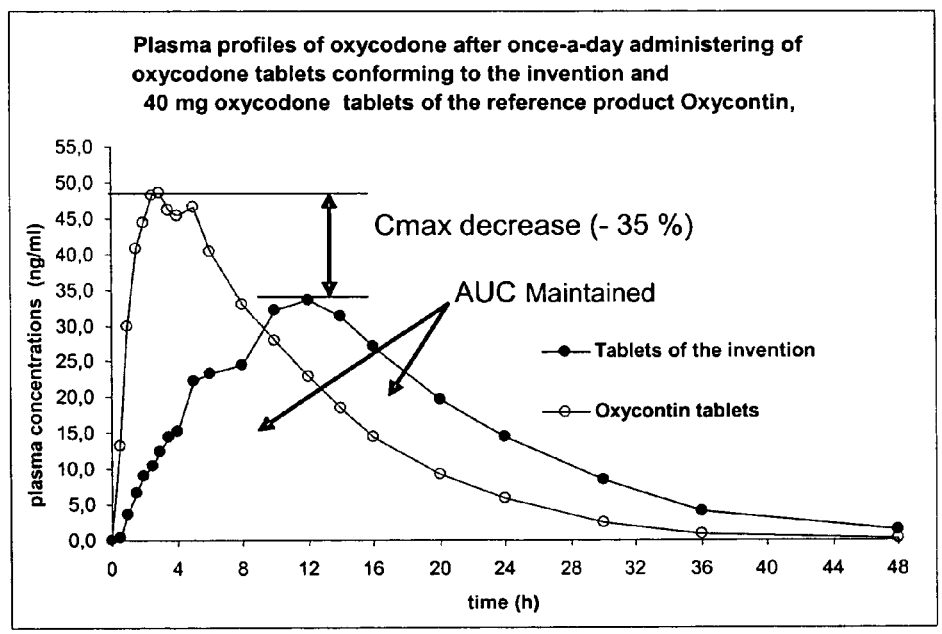

The oxycodone plasma profiles obtained are given in FIG. 8 and the parameters are grouped together in following Tables 18 and 19:

TABLE 18

| Parameter | Test (invention) | | Reference | |
|---|---|---|---|---|
| | Mean | CV | Mean | CV |
| $C_{max}$ (ng/mL) | 34.412 | 20 | 53.129 | 25.0 |
| $T_{max}$ (heures) | 10.0 | 16.6 | 3.00 | 34.3 |
| $AUC_t$ (ng h/mL) | 667.109 | 16.9 | 611.848 | 21.9 |
| $AUC_\infty$ (ng h/mL) | 679.846 | 17.1 | 614.960 | 21.7 |
| $AUC_{t/\infty}$ (%) | 98.17 | 1.7 | 99.48 | 0.3 |
| $K_{el}$ (hours$^{-1}$) | 0.1154 | 24.0 | 0.1561 | 16.4 |
| $T_{1/2\ el}$ (hours) | 6.39 | 28.0 | 4.56 | 17.2 |

Note:
For $T_{max}$ values it is the mean value which is indicated; CV: Coefficient of variation; $K_{el}$: elimination rate constant; $T_{1/2\ el}$: elimination half-life.

TABLE 19

| Parameters | Ratio | 90% confidence interval | |
|---|---|---|---|
| | | Lower | Upper |
| Cmax | 65 | 58 | 73 |
| $AUC_t$ | 110 | 104 | 116 |
| $AUC_\infty$ | 111 | 105 | 118 |

Therefore, the plasma profiles obtained show that there is no loss of bio-availability of the active ingredient, despite a decrease in Cmax.

As a result, these matrix tablets containing oxycodone conforming to the invention show a plasma profile after once-a-day administration in man such that the ratio of their Cmax to the Cmax observed after administering OxyContin® extended release tablets having the same dosage, does not exceed 0.7.

Also, these matrix tablets containing oxycodone according to the invention, have a plasma profile after once-a-day administration in man, such that the ratio of the AUC∞ observed with these tablets to the AUC∞ value observed with OxyContin® extended release tablets having the same dosage, lies within the bioequivalence interval of 80 to 125%.

These results are particularly advantageous since they mean that the oxycodone is just as well absorbed by the body as the reference product but, since its maximum concentration is reduced by around 35% in the tablets of the invention, it affords a substantial reduction in the risks of adverse effects which occur with high plasma concentrations.

EXAMPLE 5

Tablets of Oxycodone and Naloxone

5.1. Preparation of the Tablets

Tablets conforming to the invention are prepared by associating two active ingredients: oxycodone and naloxone.

Naloxone is an opiate antagonist, which inhibits the activity of oxycodone if the tablet is tampered with for administration via injection. When the tablet is taken in usual manner (oral route), the naloxone does not exert its antagonist effect since it is rapidly metabolised when ingested by oral route. The ratio of oxycodone/naloxone base used here is 4:1.

The tablets are produced in the same manner as in Example 4 (granulation of oxycodone in a high shear granulator). They do not undergo any heat treatment either before, during or after compression.

The general formula of the tablets thus manufactured (batch XCOX 5731) is summarized in Table 20 below.

TABLE 20

| Raw materials | Mg/tab | (%) |
|---|---|---|
| Granulated oxycodone | 22.66 | 12.51 |
| Naloxone 2HCl•$H_2O$ | 6.10 | 3.37 |
| Kollidon SR ® | 75.54 | 41.71 |
| Avicel pH102 ® | 75.54 | 41.71 |
| Syloïd 244 | 0.367 | 0.20 |
| Magnesium stearate | 0.91 | 0.50 |
| Total | 181.1 | 100.0 |

After compression the tablets have the physical characteristics given in following Table 21.

TABLE 21

| Description of tablet | Round, flat, white | |
|---|---|---|
| Diameter | 8 | mm |
| Thickness | 2.90 | mm |
| Mean weight | 175.8 | mg |
| Hardness | 315 | N |
| Diametral resistance | 8.6 | Mpa |

It is ascertained that, conforming to the invention, it is possible to produce tablets with very high crush resistance possibly containing two active ingredients, in particular one opioid agent and one antagonist agent blocking action of the latter in the event of administering of the tablet via intravenous route.

5.2. Dissolution Profiles

Dissolution tests are conducted, as in the preceding examples, under the following conditions: Type II paddle apparatus/100 rpm/medium pH 6.8/volume of dissolution medium: 900 mL/assay by continuous UV spectrophotometry at 225 nm/vessel width: 10 mm.

The profile is given FIG. 8.

It is found that these ultra-hard tablets show a sustained-release profile (90% of the active ingredient released after 12 hours).

EXAMPLE 6

Tablets Containing Mineral Derivatives 6.1. Preparation of the Tablets

The aim of this test is to produce tablets conforming to the invention in which mineral excipients are used as chief ingredient of the compression matrix.

Tablets are prepared containing oxycodone and dicalcium phosphate dihydrate (Emcompress®) to replace the excipients of Kollidon SR® and Avicel PH 102® type used in the preceding examples.

The preparation method is identical to the one described in Example 1 (granulation of oxycodone then physical mixing with the powdered excipients of the compression mixture).

The general production formula for these tablets (batch XCOX 5723) containing a dose of 20 mg is given in following Table 22.

TABLE 22

| Raw materials | Mg/tabl | (%) |
|---|---|---|
| Granulated oxycodone (XOXY 5634) | 22.57 | 12.90 |
| Emcompress ® | 151.21 | 86.40 |
| Syloïd 244FP | 0.35 | 0.20 |
| Magnesium stearate | 0.88 | 0.50 |
| Total | 175.00 | 100.00 |

The mixture obtained is compressed as in Example 1.

The physical characteristics of the tablets after compression are given in following Table 23:

TABLE 23

| Description of tablet | Round, flat, white |
|---|---|
| Diameter | 6 mm |
| Thickness | 3.16 mm |
| Mean weight | 178.8 mg |
| Hardness | 170 N |
| Diametral resistance | 5.7 Mpa |

It is ascertained once again that the crush resistance obtained is well above 4 MPa, even though no heating step of the mixture or of the compression tooling was necessary.

6.2. Dissolution Profile

The tablets so obtained are then placed in a dissolution medium.

The dissolution conditions are the following: Type II paddle apparatus; paddle rotating speed: 100 rpm; medium pH 6.8; volume of dissolution medium: 900 ml; continuous UV at 225 nm; vessel 10 mm.

Figure 9:
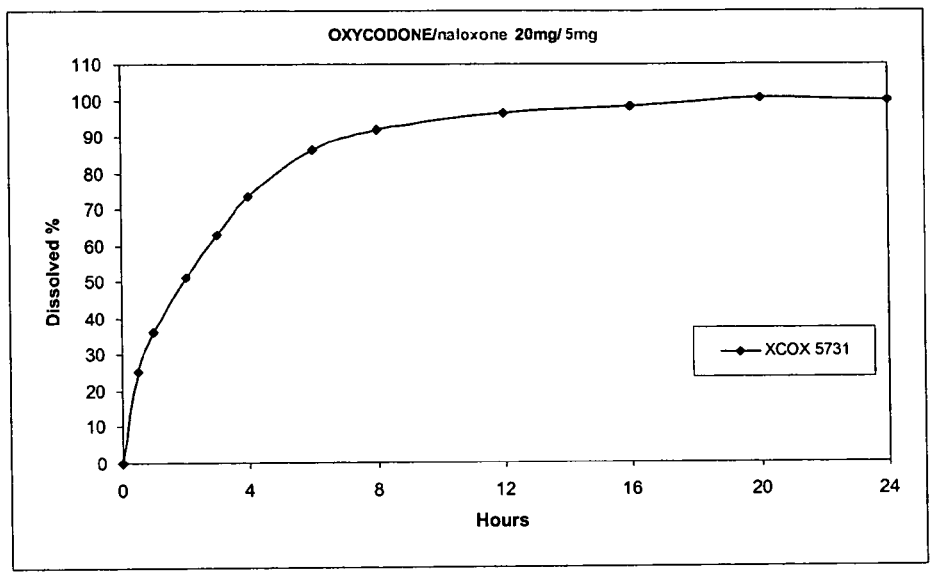
FIG. 9 illustrates the 24-hour dissolution profile, at pH 6.8, of ultra-hard, non-coated tablets of oxycodone and naloxone, according to example 5.
Figure 10:
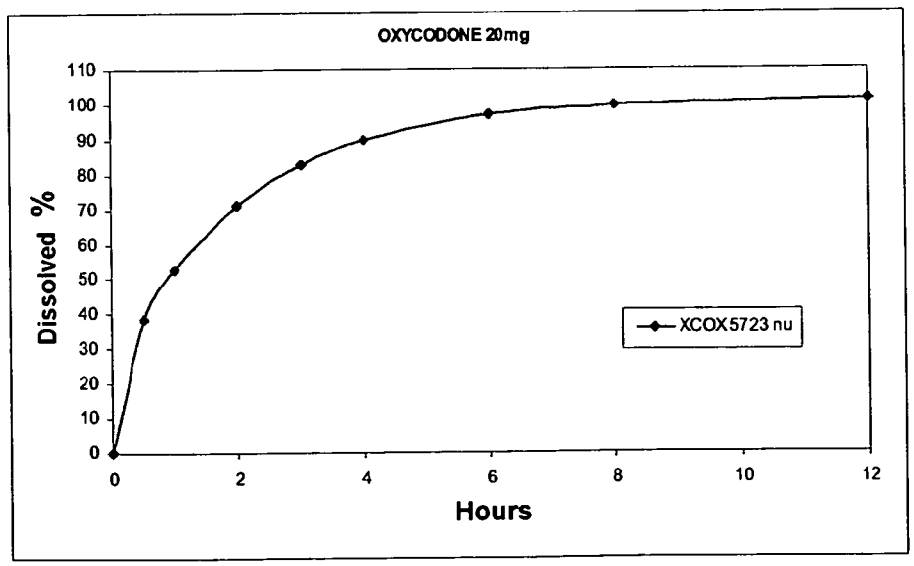
FIG. 10 illustrates the 10-hour dissolution profiles, at pH 6.8, of non-coated, ultra-hard tablets containing 20 mg oxycodone.

The results are given in FIG. 9.

It is found that the tablets conforming to the invention obtained using mineral excipients are able to release oxycodone over a relatively extended time period.

EXAMPLE 8

Drug Abuse Tests 8.1. Crush Tests

The objective of this example is to determine the difficulty in breaking or crushing and optionally obtaining a powder from the Oxycodone tablets conforming to the invention, compared with tablets of the reference oxycodone product (OxyContin®).

Four means were chosen to implement this step and placed in increasing order of difficulty:

knife (Opinel® pocket knife type)

coffee spoon combination pliers glass mortar and pestle (laboratory glassware)

Assessment of crushing difficulty was determined in relation to the hardness of the tablet.

The physical characteristics of the tested Oxycodone tablets are given in Table 24.

TABLE 24

| Tested tablet | Thickns. | Size | Shape | Wt. (mg) | Hardness (N) | Crush resistance (MPa) |
|---|---|---|---|---|---|---|
| OxyContin ® 20 mg | 3.43 | Diameter 7.24 mm | Round pink | 135.9 | 105 | 2.7 |
| Invention (20 mg) | 3.30 | Length 11.0 mm Width 5.5 mm | Oblong white | 175.9 | 467 | 8.8 |

The crush resistance of the reference tablets is 3.3 times less than that of the tablet of the invention.

The use of pliers allowed rough crushing of the tablets (pieces of 1 to 2 mm), both for the reference product and for the tablets of the invention.

After the rough crushing step using pliers, use of the laboratory mortar enabled a fine powder to be obtained in both cases. However, the use of the mortar on intact tablets conforming to the invention did not permit their crushing.

The crushing difficulty observed on each of the types of tablet in relation to the tool used is summarized in following Table 25:

TABLE 25

|  | Knife | Coffee spoon | Pliers | Mortar |
|---|---|---|---|---|
| OxyContin ® 20 mg | Easily cut, Chipping | Easy crushing | Easy crushing, chipping | Very easy crushing |
| Invention 20 mg | Difficult to cut, no crushing | Crushing impossible | Easy crushing, chipping | Crushing impossible (without prior cutting) |

The reference OxyContin® product can be crushed fairly easily, irrespective of the means used. Since it has low hardness strength, it has a tendency to chip.

On the other hand, the tablet conforming to the invention can only be crushed with combination pliers; a knife only achieves cutting but no crushing. After cutting, the pieces can be ground in a mortar.

8.2. Dissolution Tests

A tablet cut in half using a knife, and a tablet roughly crushed using pliers are subjected to a dissolution test to analyse the impact of cutting and crushing on the dissolution profile, compared with an intact tablet. This test is conducted on batch XCOX 5726 prepared following Example 4, and on the OxyContin® reference product.

The dissolution method is as follows: continuous dissolution, dissolution medium pH 6.8, 900 ml of medium per vessel, rotating paddle method, paddle rotating speed: 100 rpm, dosage: 40 mg active ingredient per vessel, vessel thickness: 10 mm; measurement by UV spectrometry (wavelength $\lambda=225$ nm). Readings are taken every 5 minutes during the first hour, then every 15 minutes up to 24 h.

Figure 11:
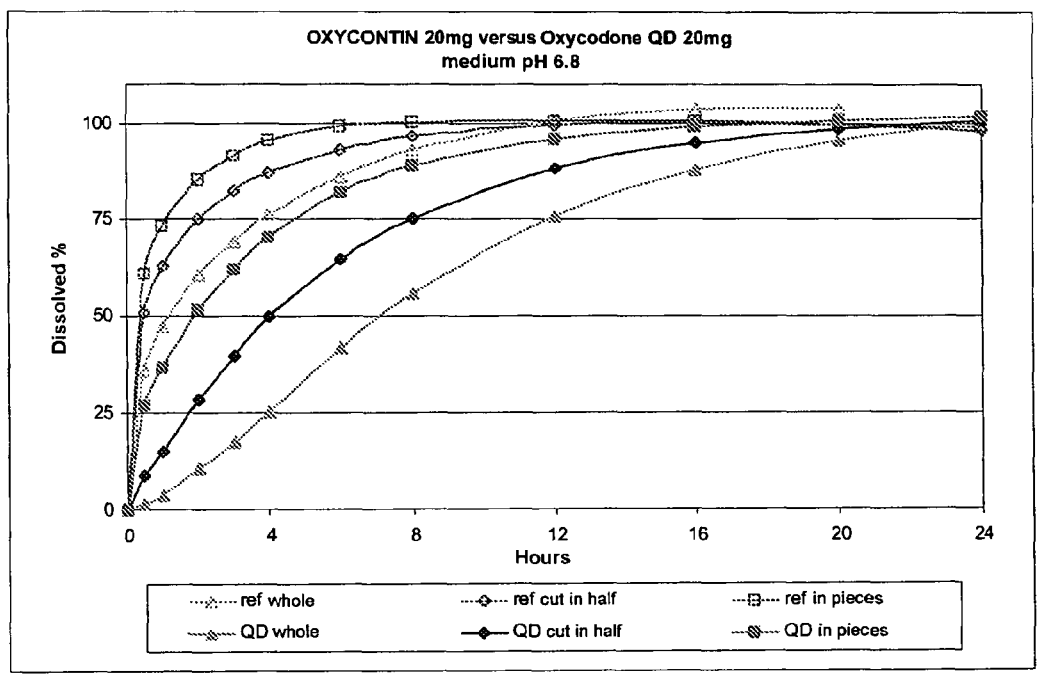
FIG. 11 illustrates the dissolution profiles observed with tablets conforming to the invention («QD») and tablets of the reference product OxyContin® (ref) at pH 6, 8, for whole tablets, tablets cut in half or crushed tablets («in pieces»)

The results obtained for dissolutions in the pH 6.8 medium are given in following Table 26 and in FIG. 11.

TABLE 26

| | OxyContin ® 20 mg batch 122810 | | | Oxycodone 20 mg XCOX 5726 | | |
|---|---|---|---|---|---|---|
| Time (h) | Whole tablet | Tablet cut in half | Tablet in pieces | Whole tablet | Tablet cut in half | Tablet in pieces |
| 0.5 | 35.9 | 50.8 | 61.0 | 1.3 | 8.6 | 26.7 |
| 1 | 47.1 | 62.8 | 73.4 | 3.7 | 15.0 | 36.5 |
| 2 | 60.5 | 75.2 | 85.4 | 10.7 | 28.2 | 51.5 |
| 3 | 69.4 | 82.3 | 91.6 | 17.3 | 39.4 | 62.2 |
| 4 | 76.2 | 87.0 | 95.4 | 24.9 | 49.7 | 70.4 |
| 6 | 86.0 | 92.9 | 99.0 | 41.7 | 64.8 | 81.9 |
| 8 | 92.8 | 96.5 | 100.3 | 55.8 | 75.3 | 88.8 |
| 12 | 100.7 | 99.4 | 100.7 | 75.7 | 88.1 | 95.9 |
| 16 | 103.4 | 100.1 | 100.5 | 87.7 | 94.7 | 99.2 |
| 20 | 103.9 | 99.4 | 99.5 | 95.3 | 98.4 | 100.7 |
| 24 | — | 98.2 | 99.2 | 100.4 | 100.5 | 101.5 |

It is ascertained that in a pH 6.8 medium, the dissolution profile of the reference product is close to that targeted for the bare tablet i.e. without a sustained-release coating, whereas the profile of the tablet of the invention («QD») is close to that targeted for a sustained-release tablet.

The cutting in half of the tablet accelerates dissolution, and acceleration is increased when the tablet is cut in pieces for both types of tablets, making the active ingredient more rapidly available for absorption via oral route.

However, the profile of the oxycodone in the crushed «QD» tablet, conforming to the invention, remains a sustained-release profile.

8.3 Evaluation of Extraction of the Active Ingredient

The tested tablets are also evaluated regarding the extraction of their active ingredient for injection.

The applicant used the so-called «Stéribox®» kit available in pharmacies and designed for drug addicts, for the purpose of preventing the transmission of pathogenic agents through the exchange of contaminated syringes.

The Stéribox® contains:
two 1 ml syringes,
two 5 ml doses of water for injection preparations,
two cups so-called «Stéricup®»
two filters Extraction of oxycodone from the reference product and from the tablet conforming to the invention is conducted as follows on each batch:
2 tests on a whole tablet,
2 tests on a tablet roughly crushed with pliers,
2 tests on a tablet of the invention crushed with pliers and then with mortar and pestle, and
2 tests on a reference tablet directly crushed in a mortar.

The tested extraction medium is the water supplied with the Stéribox®, in the maximum available volume (2 ml).

The operating mode used for extraction is the one described in the leaflet supplied with the Stéribox®:

1—place the prepared sample (whole, roughly crushed or ground) in the cup,
2—add 2 ml water using a gauged pipette,
3—mix using the plunger of the syringe for 2 minutes,
4—heat the content of the cup with a lighter for 1 minute,
5—check the remaining volume after heating: the remaining volume is 1.7 ml.
6—filter the solution using the sterile filter contained in the Steribox® and previously placed in the syringe. If necessary use a pipette to place the cup solution into the syringe,
7—dilute the filtrate in water to obtain a theoretical concentration of active ingredient of 20 mg/100 ml
8—conduct analysis replacing the extraction solvent by water for the reference product and the test product.

The results of the contents obtained and the extraction yields for each of the tests are summarized in following Table 27.

TABLE 27

| | OxyContin 20 mg batch 122810 | | | Oxycodone 20 mg XCOX 5726 | | |
|---|---|---|---|---|---|---|
| | Whole tablet | Roughly crushed tablet | Ground tablet | Whole tablet | Roughly crushed tablet | Ground tablet |
| Content obtained mg/tablet | 0.37* | 16.3 | 18.4 | 0.25 | 5.8 | 15.2 |
| CV (%) | — | 4.6 | 3.3 | 4.1 | 2.1 | 15.9 |
| Yield | 2.0% | 86.2% | 97.4% | 1.3% | 30.4% | 79.6% |

*The results concern a single test, the second test being cloudy and the result unusable.

It is found that the extraction yield is low with a whole tablet, irrespective of the tablet used.

However, extraction yields are higher for OxyContin® in all tests. In particular, when the tablet conforming to the invention is roughly crushed, it releases close to 5 times less active ingredient than the reference product used under the same conditions.

These results show that abuse by intravenous route can be achieved more easily with OxyContin® than with the oxycodone «QD» tablets of the invention.

Only pliers are required to obtain good extraction of Oxy-Contin® whereas for the Oxycodone «QD» tablets of the invention an additional tool is required to achieve efficient crushing and thereby increase extraction yield. The tablets conforming to the invention are therefore particularly effective to deter drug abuse of opioid active ingredients.

The invention claimed is:

1. Water-insoluble, matrix tablets comprising oxycodone or one of its pharmaceutically acceptable salts, capable of releasing oxycodone into the body over an extended time period and comprising oxycodone within a compression matrix, said matrix comprising a mixture of microcrystalline cellulose and polyvinyl acetate/polyvinylpyrrolidone (80:20) to the proportion of (1:1), magnesium stearate as an anti-adherent agent, a cellulose derivative as a binder, and one or more of the following substances (a) to (f) or a mixture thereof:
   (a) a substance which irritates the nasal and/or pharyngeal tracts,
   (b) a viscosity-increasing agent, leading to formation of a gel when the tablet is dissolved in a minimum amount of water,
   (c) an emetic substance,
   (d) an aversive coloring agent,
   (e) a bittering-substance,
   (f) an antagonist of the active ingredient (s) which may be the subject of drug abuse wherein said matrix represents 50-98% in weight of the total weight of the tablets, and wherein said matrix tablets have a cured outercoating.

2. Matrix tablets according to claim 1, wherein neither the mixture to be compressed, nor the compression tooling are subjected to a heating step either before or during the actual compression step.

3. Matrix tablets according to claim 1, wherein said compression matrix represents 85 to 95% weight % of the total weight of said tablet.

4. Matrix tablets according to claim 1, wherein said compression matrix also comprises at least one pharmaceutically acceptable excipient selected from the group consisting of anti-adherent agents, agents able to improve tablet cohesion on compressing, fillers, lubricants, plasticizers, bulking agents, sweeteners and colouring agents.

5. Matrix tablets according to claim 1, wherein the antagonist agent of the said active ingredient(s) which may be the subject of drug abuse is naloxone or naltrexone or one of their pharmaceutically acceptable salts.

6. Matrix tablets according to claim 1, wherein said outer coating comprises at least one sustained-release polymer advantageously chosen from the group comprising ethylcellulose derivatives and methacrylic polymers.

7. Matrix tablets according to claim 1, wherein the outer coating consists of ethylcellulose.

8. Matrix tablets according to claim 1, wherein said tablets are capable of releasing oxycodone over a period of more than 12 hours.

9. Matrix tablets according to claim 1, wherein said tablets are capable of releasing oxycodone over a period of more than 20 hours.

10. Matrix tablets according to claim 1, wherein said tablets have a plasma profile after once-a-day administration in man, such that the ratio of the Cmax observed after administration of said tablets to the Cmax value observed after administration of oxycodone extended release tablets containing the same dose, does not exceed 0.7.

11. Matrix tablets containing oxycodone according to claim 1, wherein a plasma profile after once-a-day administration in man is such that the ratio of AUC$\infty$ observed for said tablets to the AUC $\infty$ value observed with oxycodone extended release tablets with the same dose, lies in the interval of 80 to 125%.

12. Tablets according to claim 1, wherein said tablets can be administered once a day.

13. Matrix tablets according to claim 1, wherein the two polymers microcrystalline cellulose and polyvinyl acetate/polyvinylpyrrolidone (80:20) each represent a weight proportion in the order of 40% of the total weight of said compression matrix.

* * * * *